United States Patent [19]

Hemmerling et al.

[11] Patent Number: 5,354,500

[45] Date of Patent: * Oct. 11, 1994

[54] OPTICALLY ACTIVE CARBOXYLIC ESTERS OF OXYGEN-CONTAINING HETEROCYCLES AS DOPING SUBSTANCES IN LIQUID CRYSTAL MIXTURES AND LIQUID CRYSTAL MIXTURES CONTAINING THEM

[75] Inventors: Wolfgang Hemmerling, Sulzbach; Ingrid Müller, Hofheim am Taunus; Hans-Rolf Dübal, Königstein; Claus Escher, Mühltal; Gerhard Illian, Frankfurt am Main; Mikio Murakami, Königstein; Dieter Ohlendorf, Liederbach; Rainer Wingen, Hattersheim am Main, all of Fed. Rep. of Germany

[73] Assignee: Hoechst Aktiengesellschaft, Frankfurt am Main

[*] Notice: The portion of the term of this patent subsequent to Jan. 29, 2008 has been disclaimed.

[21] Appl. No.: 870,111

[22] Filed: Apr. 17, 1992

Related U.S. Application Data

[63] Continuation of Ser. No. 410,829, Sep. 22, 1989, abandoned, and a continuation-in-part of Ser. No. 199,101, May 26, 1988, Pat. No. 4,988,459.

[30] Foreign Application Priority Data

May 29, 1986 [DE] Fed. Rep. of Germany ....... 3718174
Sep. 24, 1988 [DE] Fed. Rep. of Germany ....... 3832502

[51] Int. Cl.$^5$ .............................................. C09K 19/34
[52] U.S. Cl. ............................. 252/299.61; 544/238; 544/241; 544/296; 544/315; 544/318; 544/334; 544/335; 544/357; 544/408; 544/409; 546/256; 546/258; 546/263; 546/286; 546/288; 546/289; 546/290; 252/299.6
[58] Field of Search ............ 252/299.01, 299.6, 299.61, 252/299.63; 544/238, 241, 296, 315, 318, 334, 335, 357, 408, 409; 546/256, 258, 263, 286, 288, 289, 290; 549/370, 371, 372, 373, 374, 375, 448, 450, 453, 454, 455, 550, 551, 553, 554, 560, 561, 562

[56] References Cited

U.S. PATENT DOCUMENTS

| | | | |
|---|---|---|---|
| 4,638,073 | 1/1987 | Walba et al. | 252/299.61 |
| 4,988,459 | 1/1991 | Scherowsky et al. | 252/299.61 |

FOREIGN PATENT DOCUMENTS

| | | |
|---|---|---|
| 0233602 | 8/1987 | European Pat. Off. . |
| 0263437 | 4/1988 | European Pat. Off. . |
| 0275522 | 7/1988 | European Pat. Off. . |
| 0288813 | 11/1988 | European Pat. Off. . |
| 3713273 | 11/1988 | Fed. Rep. of Germany . |
| 3718174 | 12/1988 | Fed. Rep. of Germany . |

OTHER PUBLICATIONS

Sequin, V., Helvetica Chimica Acta–vol. 64, Fasc. 8, (1981), pp. 2654–2664.

(List continued on next page.)

*Primary Examiner*—Philip Tucker
*Attorney, Agent, or Firm*—Curtis Morris & Safford

[57] ABSTRACT

Use of optically active carboxylic esters of oxygen-containing heterocycles as doping substances in liquid crystal mixtures and liquid crystal mixtures containing them. Optically active 1,3-dioxolane-4-carboxylic esters and oxirane-2-carboxylic esters of the general formula (I)

$$R(-A^1)_j(-M^1)_k(-A^2)_l(-M^2)_m(-A^3)_n-X-Ac$$

in which
$R^1$ is, for example, $(C_1-C_{16})$-alkyl or $(C_1-C_{16})$-alkoxy,
$A^1$, $A^2$, $A^3$ are, for example, phenyl or pyrimidine-2,5-diyl,
$M^1$, $M^2$ are, for example, CO—O, $CH_2$—$CH_2$,
j, l are 0, 1, 2,
k, m are 0, 1,
n is 0, 1, 2,
X is O, S and
Ac is

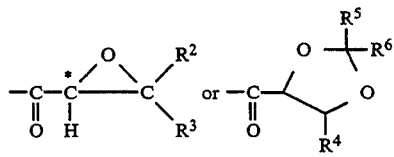

in which $R^2$, $R^3$, $R^4$, $R^5$, $R^6$ for example, H or methyl, are particularly suitable doping substances for liquid crystalline mixtures, since they induce a high spontaneous polarization and effect a substantial decrease in the melting point.

7 Claims, No Drawings

OTHER PUBLICATIONS

Newman, et al., "The Conversion of Phenols to Thiophenols via Dialkylthiocarbamates", J. Org. Chem. 31, 3980 (1966).

Mitsunobu, "The Use of Diethyl Azodicarboxylate and Triphenylphosphine in Synthesis and Transformation of Natural Products", Synthesis, 1 (1981).

Corriu et al., "Activation of Grignard Reagents by Transition-metal Complexes. A New and Simple Synthesis of trans-Stilbenes and Polyphenyls", J. Chem. Soc., Chem. Comm., 144 (1972).

Tamao et al., "Selective Carbon–Carbon Bond Formation by Cross-Coupling of Grignard Reagents with Organic Halides", J. Am. Chem. Soc. 94, 4374 (1972).

Tamao et al., "Stereochemistry of the nickel-catalyzed cross-coupling reaction of Grignard reagents with olefinic halides: stereospecific *versus* nonstereospecific-stereoselective reactions", J. Organomet. Chem. 55, C 91 (1973).

OPTICALLY ACTIVE CARBOXYLIC ESTERS OF OXYGEN-CONTAINING HETEROCYCLES AS DOPING SUBSTANCES IN LIQUID CRYSTAL MIXTURES AND LIQUID CRYSTAL MIXTURES CONTAINING THEM

This application is a continuation of application Ser. No. 07/410,829, filed Sep. 22, 1989, now abandoned and is a continuation-in-part of U.S. application Ser. No. 07/199,101, filed May 26, 1988, now U.S. Pat. No. 4,988,459.

DESCRIPTION

Use of optically active carboxylic esters of oxygen-containing heterocycles as doping substances in liquid crystal mixtures and liquid crystal mixtures containing them Earlier, yet non-prior publications DE-A 3,713,273 and 3,718,174 describe optically active 1,3-dioxolane-4-carboxylic esters and oxirane-2-carboxylic esters which can be represented by the following general formula (I):

$$R^1(-A^1)_j(-M^1)_k(-A^2)_l(-M^2)_m(-A^3)_n-X-Ac \quad (I)$$

in which $R^1$ is —X—AC; H; a straight-chain or branched alkyl or alkyloxy chain having 1–16 carbon atoms; a straight-chain or branched alkenyl or alkenyloxy chain having 3–16 carbon atoms, it being possible for one or more non-adjacent —CH$_2$— groups to be replaced by —O—, —S—, —CO—, —O—CO— or —CO—O— and one or more hydrogen atoms to be replaced by F, Cl, Br or CN; or $R^1$ is F, Cl, Br or CN, —$A^1$, —$A^2$ are

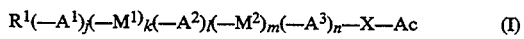

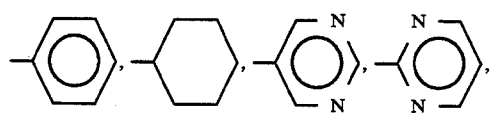

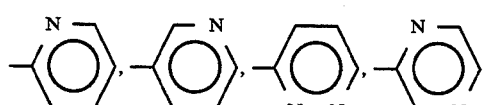

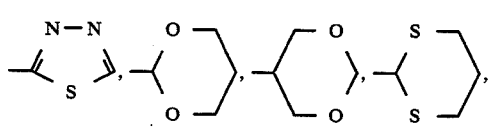

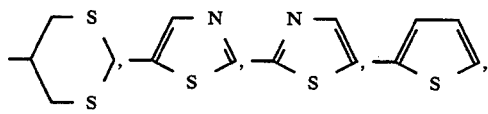

—$A^3$ is

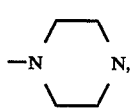

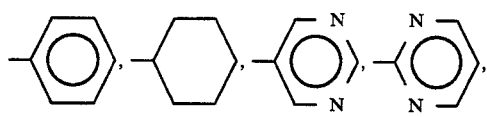

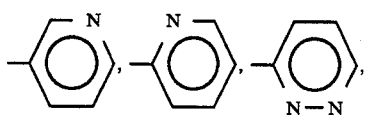

—$M^1$, —$M^2$ are —CO—O, —O—CO, —CH$_2$CH$_2$, —CH=CH, —CH$_2$O, —OCH$_2$, j and l are zero, 1 or 2,
k and m are zero or 1,
n is zero, 1 or 2,
with the following proviso: if j and/or l are zero, k is zero; if n is zero, m is zero; the sum of j+l+n is at least 1 and at most 3,
X is oxygen or sulfur,
Ac is the acyl radical of an oxirane-2-carboxylic acid (II)

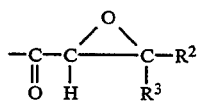

or of a 1,3-dioxolane-4-carboxylic acid (III)

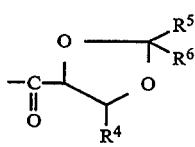

where $R^2$ is H or $C_1$–$C_{16}$-alkyl or cyclohexyl or bicyclohexyl, each of which can also be substituted in the 4- or 4'-position by an alkyl chain of 1 to 16 carbon atoms, $R^3$ is H or alkyl having 1 to 16 carbon atoms, $R^4$ is H or an alkyl radical having 1 to 10, or an alkenyl radical having 2 to 10, carbon atoms, $R^5$ and $R^6$ are each H or an alkyl radical having 1 to 10 carbon atoms, in which one or more hydrogen atoms of the alkyl radical can be replaced by F, or $R^2$ and $R^3$ together with the C (2) atom of the dioxolane ring form a cyclopentane, cyclohexane or cycloheptane ring.

The optically active carboxylic esters, according to the invention, of heterocycles containing oxygen in the terminal acyl radical are compounds in which at least one of the radicals —$A^1$, —$A^2$ and —$A^3$ is at least monosubstituted by F, Cl, Br, CN and/or a lateral alkyl or alkyloxy group having 1 to 10 carbon atoms.

These compounds are obtained by reaction of oxirane-2-carboxylic acids of the formula (IIa) or 1,3-dioxolane-4-carboxylic acids of the formula (IIIa)

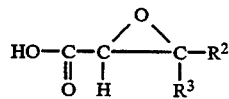

-continued

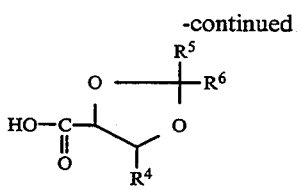
(IIIa)

or their derivatives which are capable of ester formation with compounds (IV)

$$R^1(-A^1)_j(-M^1)_k(-A^2)_l(-M^2)_m(-A^3)_n-XH \quad (IV)$$

in a manner known per se.

They serve in particular as doping substances for manufacturing ferroelectric liquid crystal mixtures. In tilted smectic liquid crystal phases, they induce a high spontaneous polarization and effect a substantial decrease in the melting point. The esters according to the invention furthermore have a large negative $\Delta\epsilon$, i.e. they are dielectrically negative.

Particularly suitable optically active esters of the formula (I) are those in which
$-A^1, -A^2, -A^3$ are

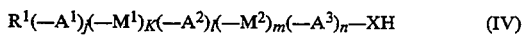

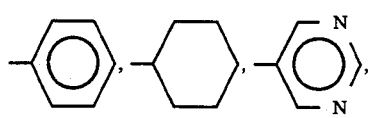

—$M^1$, $M^2$ are —CO—O, —O—CO, —CH$_2$O, —OCH$_2$,
X is oxygen,
Ac is the acyl radical of an oxirane-2-carboxylic acid of the formula (II) or of a 1,3-dioxolane-4-carboxylic acid of the formula (III) and
$R^1$, $R^2$, $R^3$, $R^4$, $R^5$, $R^6$, j, k, l, m, n have the abovementioned meanings.

The liquid crystal mixtures according to the invention are composed of 2 to 20, preferably 2 to 15, components, among them at least one of the chiral doping substances claimed according to the invention.

The other components are preferably selected from the known compounds which have nematic, cholesteric and/or smectic phases; these include, for example, Schiff bases, biphenyls, terphenyls, phenylcyclohexanes, cyclohexylbiphenyls, N-, S- or O-containing heterocycles, for example pyrimidines, cinnamic esters, cholesterol esters or differently bridged, polynuclear esters, which have polar end groups, of p-alkylbenzoic acids. In general, the commercially available liquid crystal mixtures are present as mixtures of a large range of components even before the optically active compound(s) is(are) added, at least one of which is mesogenic, i.e. as a compound which in its derivatized form or in a mixture with certain cocomponents shows a liquid crystal phase, which may be expected to form at least one enantiotropic (clear point < melting point) or monotropic (clear point > melting point) mesophase.

EXAMPLE 1

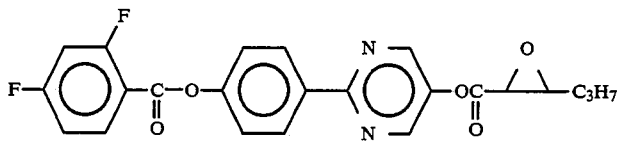

(2R, 3R)-[2-(4-(2,4-Difluorobenzoyloxy)phenyl)pyrimidin-5-yl]3-propyloxirane-2-carboxylate 984 mg (3 mmol) of [4-(5-hydroxypyrimidin-2-yl)phenyl]2,4-difluorobenzoate are initially introduced into 25 ml of dichloromethane. 680 mg(3.3 mmol) of dicyclohexylcarbodiimide, 430 mg of (2R,3R)-3-propyloxirane-2-carboxylic acid and 40 mg of dimethylaminopyridine were added to the stirred suspension, and stirring at room temperature was continued for 20 hours. After chromatography and several recrystallizations, colorless crystals of m.p. 94.1° C. at 64.2 J/g are obtained.

$[\alpha]_D^{25} = -14.8°$ (c=2, CHCl$_3$)

In a non-chiral test mixture which has the phase sequence C12.5S$_c$83S$_A$95N100 I, the compound has a spontaneous polarization of 9 nC/cm$^2$ at 60° C. at a doping level of 5 mol %.

The following were synthesized analogously:

EXAMPLE 2

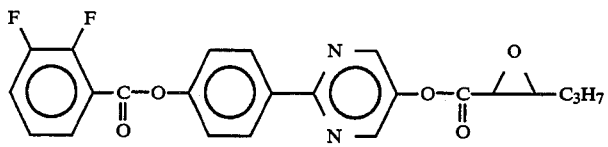

(2R, 3R)-[2-(4-(2,3-Difluorobenzoyloxy) phenyl)pyrimidin-5-yl]3-propyloxirane-2-carboxylate m.p. 97° C. at 70 J/g $[\alpha]_D^{25} = -10°$ (c=2, CHCl$_3$)
Spontaneous polarization: 19 nC/cm$^2$

EXAMPLE 3

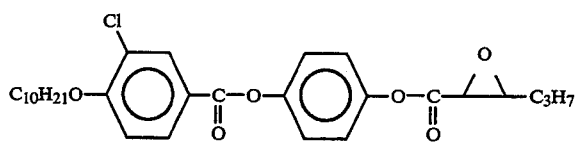

(2R, 3R)-[4-(3-Chloro-4-decyloxybenzoyloxy)phenyl] 3-propyloxirane- 2-carboxylate m.p. 66.4° C. at 61.2 J/g $[\alpha]_D^{25} = -73°$ (c=2, CHCl$_3$)
Spontaneous polarization: 14.5 nC/cm$^2$

EXAMPLE 4

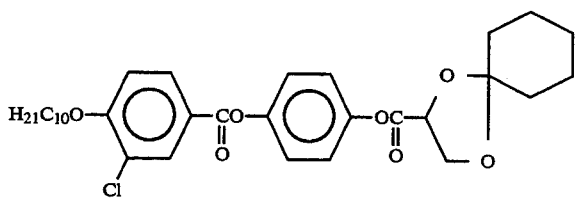

(4R)-[4-(3-Chloro-4-decyloxybenzoyloxy) phenyl] 2,2-pentamethylene-1,3-dioxolane-4-carboxylate 1.6 ml of triethylamine are added to a solution of 4.6 g of 4-[4-(3-chloro-4-decyloxybenzoyloxy)phenol] in 50 ml of tetrahydrofuran. After cooling to 0° C., a solution of 2.33 g of (4R)-2,2-pentamethylene-1,3-dioxolane-4-carbonyl chloride in 15 ml of tetrahydrofuran is added over a period of 5 minutes. After 2 hours, the mixture is filtered, the filtrate is evaporated to dryness, and the residue is purified by chromatography (SiO$_2$, dichloromethane/ethyl acetate 97:3). The product is further purified by recrystallization from hexane.

m.p. 81.3° C. at 69.1 J/g $[\alpha]_D^{22}$: +10.2° (c=2.5, CH$_2$Cl$_2$)

In a non-chiral test mixture which has the phase sequence C12.5S$_C$83S$_A$95$_N$100 I, the compound has a spontaneous polarization of 25 nC/cm$^2$ at 40° C. at a doping level of 10 mol %.

The following are prepared analogously:

EXAMPLE 5

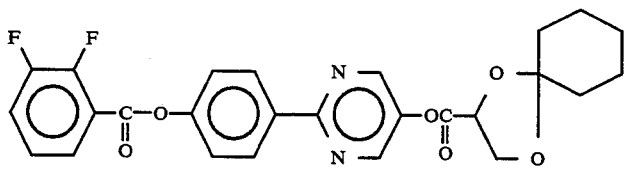

(4R)-[2-[4-(2,3-Difhorobenzoyloxy]phenyl)pyrimidin-5-yl]2,2-pentamethylene-1,13-dioxolane-4-carboxylate m.p. 140.7° C. at 79.5 J/g $[\alpha]_D^{22}$: +10.6° (c=2.7, CH$_2$Cl$_2$) Spontaneous polarization: 9.5 nC/cm$^2$ at 60° C. (10 mol %)

EXAMPLE 6

(4R)-[2-(4-[2,4-Difhorobenzoyloxy]phenyl)pyrimidin-5-yl]2,2-pentamethylene-1,13-dioxolane-4-carboxylate m.p. 161° C. at 83.1 J/g $[\alpha]_D^{22}$: +14.5° (c=2.7, CH$_2$Cl$_2$)

The following are obtained analogously to Example 1:

EXAMPLE 7

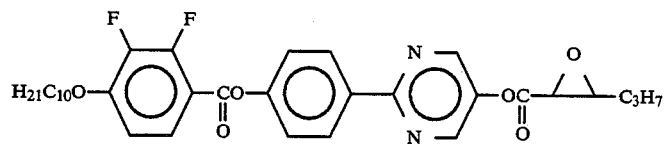

(2R,3R)-[2-(4-Decyloxy-2,3-difluorobenzoyloxy) phenyl-pyrimidin-5-yl]3-propyloxirane-2-carboxylate m.p. 119° C. $[\alpha]_D^{25}$: −12.8° (c=2, CH$_2$Cl$_2$)

EXAMPLE 8

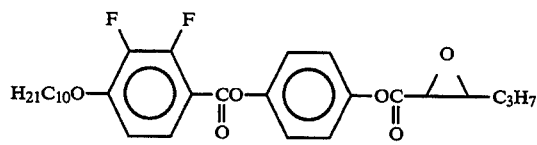

(2R,3R)- [4-(4-Decyloxy-2,3-difluorobenzoyloxy)-phenyl]3-propyloxirane-2-carboxylate $[\alpha]_D^{25}$: −12.9° (c=2, CH$_2$Cl$_2$) Phase sequence: X 55 I The following are obtained analogously to Example 4:

EXAMPLE 9

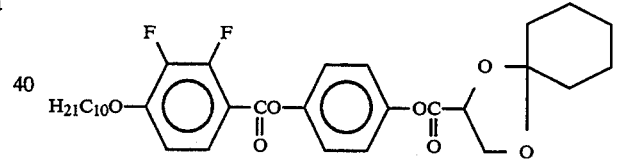

(4R)-[4-(4-Decyloxy-2,3-difluorobenzoyloxy)-phenyl]2,2-pentamethylene-1,3-dioxolane-4-carboxylate m.p. 86.7° C. $[\alpha]_D^{25}$: +10.6° (c=2.5, CH$_2$Cl$_2$)

EXAMPLE 10

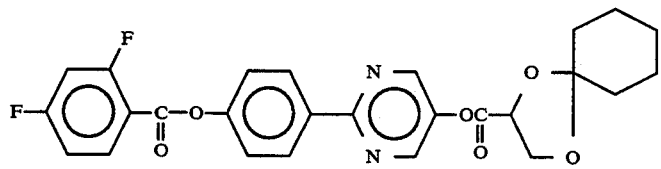

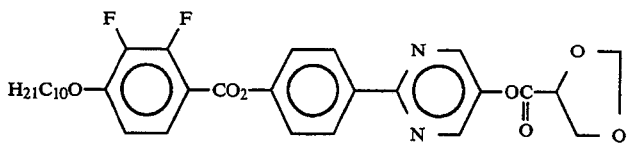

(4R)-[2-(4-Decyloxy-2,3-difluorobenzoyloxy)phenyl-pyrimidin-5-yl]2,2-pentamethylene-1,3-dioxolane-4-carboxylate $[\alpha]_D^{25}$: −12.8° (c=2, CH$_2$Cl$_2$) Phase sequence C(104S$_x$133) 149 N* 162 I

Working Example 1 a) A ferroelectric liquid-crystalline mixture is composed of 6 components 5-octyloxy-2-(4-butyloxyphenyl)-pyrimidine 25.4 mol %
5-octyloxy-2-(4-hexyloxyphenyl)-pyrimidine 24.1 mol %
5-octyloxy-2-(4-octyloxyphenyl)-pyrimidine 11.1 mol %
5-octyloxy-2-(4-decyloxyphenyl)-pyrimidine 20.2 mol %
[4-(5-decylpyrimidin-2-yl)phenyl]trans-4- 14.2 mol % pentylcyclohexanecarboxylate
(2R,3R)-[2-(4-decyloxy-2,3-difluorobenzoyloxy) phenylpyrimidin-5-yl]3-propyloxirane-2-carboxylate 5 mol % and has the following liquid-crystalline phase ranges:

S$_c$* 81 N* 103 I and has a spontaneous polarization of 36 nC.cm$^{-2}$ and a switching time of 42.6 μs at 40° C.

b) In comparison, the liquid-crystalline mixture which is claimed in DE 3,831,226.3 and differs from the above-mentioned ferroelectric mixture only by not containing any doping substance has the following phase ranges S$_c$ 84 S$_A$ 93 N 105 I

Working Example 2 a) A ferroelectric liquid-crystalline mixture is composed of 6 components 5-octyloxy-2-(4-butyloxyphenyl)pyrimidine 24 mol %
5-octyloxy-2-(4-hexyloxyphenyl)pyrimidine 22.8 mol %
5-octyloxy-2-(4-octyloxyphenyl)pyrimidine 10.5 mol %
5-octyloxy-2-(4-decyloxyphenyl)pyrimidine 19.2 mol %
[4-(5-decylpyrimidin-2-yl)phenyl]trans- 4-pentylcyclohexanecarboxylate 13.5 mol %
(2R,3R)-[4-(4-decyloxy-2,3-difluorobenzoyloxy)-phenyl]3-propyloxirane-2-carboxylate 10 mol % and has the following liquid-crystalline phase ranges:

S$_c$* 73 S$_A$* 81 N* 94 I and has a spontaneous polarization of 38 nC.cm$^{-2}$ and a switching time of 23.2 μs at 40° C.

b) In comparison, the liquid-crystalline mixture which is claimed in DE 3,831,226.3 and differs from the above-mentioned ferroelectric mixture only by not containing any doping substance has the following phase ranges S$_c$ 84 S$_A$ 93 N 105 I

We claim:

1. An optically active doping substance for liquid crystal mixtures, which comprises a compound of the formula (I)

$$R^1(-A^1)_j(-M^1)_k(-A^2)_l(-M^2)_m(-A^3)_n-X-Ac \quad (I)$$

in which

R$_1$ is —X—Ac; H; a straight-chain or branched alkyl or alkyloxy chain having 1–16 carbon atoms; a straight-chain or branched alkenyl or alkenyloxy chain having 3–16 carbon atoms, it being possible for one or more non-adjacent —CH$^2$—groups to be replaced by —O—, —S—, —CO—, —O—CO— or —CO—O— and one or more hydrogen atoms to be replaced by F, Cl, Br or CN; or R$^1$ is F, Cl, Br or CN, —A$^1$, —A$^2$ are

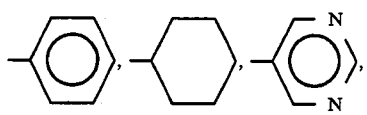

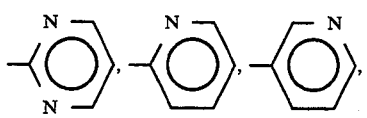

—A$^3$ is

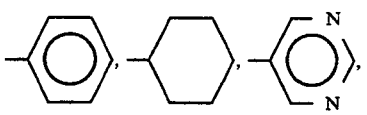

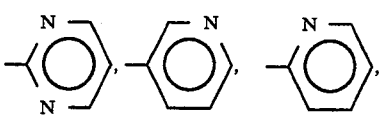

—M$^1$, —M$^2$ are —CO—O, —O—CO,
j and l are zero, 1 or 2,
k and m are zero or 1,
n is zero, 1 or 2,
with the following proviso: if j and/or l are zero, k is zero; if n is zero, m is zero; the sum of j+l+n is 2 or 3,
x is oxygen,
Ac is the acyl radical of an oxirane-2-carboxylic acid (II)

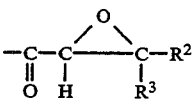

(II)

or of a 1,3-dioxolane-4-carboxylic acid (III)

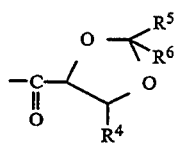
(III)

where
- $R^2$ is H or $C_1$–$C_{16}$-alkyl or cyclohexyl or bicyclohexyl, each of which can also be substituted in the 4- or 4'-position by an alkyl chain of 1 to 16 carbon atoms,
- $R^3$ is H or alkyl having 1 to 16 carbon atoms,
- $R^4$ is H or an alkyl radical having 1 to 10, or an alkenyl radical having 2 to 10, carbon atoms,
- $R^5$ and $R^6$ are each H or an alkyl radical having 1 to 10 carbon atoms, in which one or more hydrogen atoms of the alkyl radical can be replaced by F, or $R^2$ and $R^3$ together with the C (2) atom of the dioxolane ring form a cyclopentane, cyclohexane or cycloheptane ring, with the proviso that at least one of the radicals —$A^1$, —$A^2$ and —$A^3$ is at least monosubstituted by F, or Cl.

2. An optically active compound of the formula (I) in which the symbols have the following meanings:
—$A^1$, —$A^2$, —$A^3$ are

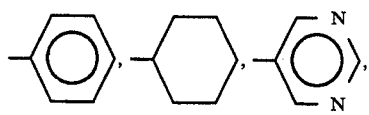

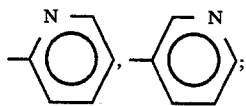

—$M^1$, $M^2$ are —CO—O, —O—CO, —$CH_2$O, —O$CH_2$,

X is oxygen,

Ac is the acyl radical of an oxirane-2-carboxylic acid of the formula (II) or of a 1,3-dioxolane-4-carboxylic acid of the formula (III) and $R^1$, $R^2$, $R^3$, $R^4$, $R^5$,$R^6$, j, k, l, m, n have the meanings mentioned in claim 1.

3. An optically active compound of the formula (I) as claimed in claim 2, wherein Ac is the acyl radical of an oxirane-2-carboxylic acid of the formula (II).

4. A liquid crystal mixture containing at least one ester of the formula (I) as claimed in claim 1.

5. A liquid crystal mixture containing at least one ester of the formula (I) as claimed in claim 2.

6. A liquid crystal mixture containing at least one ester of the formula (I) as claimed in claim 3.

7. (2R,3R)-[2-(4-Decyloxy-2,3-difluorobenzoyloxy)-phenylpyrimidin-5-yl] 3-propyloxirane-2-carboxylate.

* * * * *